US010095025B2

(12) United States Patent
Iwane

(10) Patent No.: US 10,095,025 B2
(45) Date of Patent: Oct. 9, 2018

(54) OPTICAL UNIT, ENDOSCOPE APPARATUS, AND MANUFACTURING METHOD OF OPTICAL UNIT

(71) Applicant: FUJIFILM Corporation, Tokyo (JP)

(72) Inventor: Hiroyuki Iwane, Kanagawa (JP)

(73) Assignee: FUJIFILM Corporation, Tokyo (JP)

(*) Notice: Subject to any disclaimer, the term of this patent is extended or adjusted under 35 U.S.C. 154(b) by 973 days.

(21) Appl. No.: 14/473,723

(22) Filed: Aug. 29, 2014

(65) Prior Publication Data
US 2015/0065796 A1 Mar. 5, 2015

(30) Foreign Application Priority Data

Sep. 2, 2013 (JP) .................. 2013-181401

(51) Int. Cl.
| A61B 1/00 | (2006.01) |
| G02B 27/00 | (2006.01) |
| G02B 23/24 | (2006.01) |
| B23K 1/002 | (2006.01) |
| B23K 1/008 | (2006.01) |
| B23K 1/012 | (2006.01) |
| A61B 1/05 | (2006.01) |
| A61B 1/06 | (2006.01) |

(52) U.S. Cl.
CPC ........ G02B 27/0006 (2013.01); A61B 1/0011 (2013.01); A61B 1/00096 (2013.01); B23K 1/002 (2013.01); B23K 1/008 (2013.01); B23K 1/012 (2013.01); G02B 23/2423 (2013.01); A61B 1/05 (2013.01); A61B 1/06 (2013.01)

(58) Field of Classification Search
CPC . A61B 1/0008; A61B 1/00096; A61B 1/0011; A61B 1/00174; A61B 1/00179; G02B 23/2423
See application file for complete search history.

(56) References Cited

U.S. PATENT DOCUMENTS 5,235,965 A * 8/1993 Hiroya ................ A61B 1/0008
600/108
6,955,644 B2 * 10/2005 Forkey ............... A61B 1/00142
600/101

FOREIGN PATENT DOCUMENTS

| JP | 2008-257243 A | 10/2008 | |
| JP | 2011-218033 A | * 4/2011 | .......... A61B 1/0011 |
| JP | 2011-218033 A | 11/2011 | |

OTHER PUBLICATIONS

Japanese Office Action for Japanese Application No. 2013-181401, dated Sep. 15, 2015, with an English translation.

* cited by examiner

*Primary Examiner* — Timothy J Neal
*Assistant Examiner* — Aaron B Fairchild
(74) *Attorney, Agent, or Firm* — Birch, Stewart, Kolasch & Birch, LLP

(57) ABSTRACT

An optical unit includes: a cylindrical member whose thickness varies in a circumferential direction; a transparent member disposed at one end, in an axial direction, of the cylindrical member; and a joining member which joins the transparent member to the cylindrical member and thereby seals the cylindrical member at the one end in the axial direction, and a portion, joining a side surface of the transparent member to an inner circumferential surface of the cylindrical member, of the joining member is thicker at a position where the cylindrical member is thick than at a position where the cylindrical member is thin.

6 Claims, 10 Drawing Sheets

OPTICAL UNIT, ENDOSCOPE APPARATUS, AND MANUFACTURING METHOD OF OPTICAL UNIT

CROSS-REFERENCE TO RELATED APPLICATIONS

This application claims the benefit of Japanese Patent Application JP 2013-181401, filed Sep. 2, 2013, the entire content of which is hereby incorporated by reference, the same as if set forth at length.

FIELD OF THE INVENTION

The present invention relates to an optical unit, an endoscope apparatus, and a manufacturing method of an optical unit.

BACKGROUND OF THE INVENTION

An optical unit in which imaging optical members for taking an observation image or illumination optical members for emitting illumination light are housed in a cylindrical member is provided in a tip portion of an endoscope insertion unit, to be inserted into a subject body, of endoscope apparatus. With the recent miniaturization and increase in the number of recording pixels of solid-state imaging devices, the accuracy (working errors and assembling errors) that is required in attaching such an optical unit to the tip portion of an endoscope insertion unit has become higher. This is because an image failure such as a half blur or an illumination failure may occur if the optical unit is placed in the tip portion of the endoscope insertion unit at a position that is deviated from a regular position.

In view of the above, a technique has been proposed in which the optical axis of the optical unit is deviated from the center line of the outer circumferential surface of the cylindrical member of the optical unit and the position of the optical axis is fine-adjusted with respect to the tip portion of the endoscope insertion unit by rotating the optical unit in attaching it to the tip portion of the endoscope insertion unit (refer to JP-A-2008-257243, for example).

SUMMARY OF THE INVENTION

In medical endoscope apparatus, it is necessary to disinfect or sterilize the endoscope main body that has been used, that is, inserted into the body cavity of a subject (subject body). Previously, such disinfecting and sterilizing treatment was carried out using a disinfectant solution or a sterilizing gas. However, the management and disposal of a disinfectant solution are factors in causing cost increase and the use of sterilizing gases has come to be restricted strictly in many countries for preventing pollution of the environment. In these circumstances, autoclaving (high-pressure, high-temperature steam sterilizing treatment) which does not require complicated work, enables use of the endoscope main body immediately after its sterilization, and is low in running cost is now becoming the mainstream of the treatment for disinfecting or sterilizing endoscope instruments. A typical condition of the autoclaving is such that a sterilization process is carried out at 132° C. for 4 to 10 minutes.

However, the optical unit disclosed in JP-A-2008-257243 has a problem that when it is exposed to a high-temperature atmosphere in autoclaving as mentioned above, a transparent member such as a cover glass which is provided at the tip of the optical unit may peel off the cylindrical member, in which case airtightness is no longer secured. This results from the fact that the thickness of the cylindrical member of the optical unit is not uniform in the circumferential direction. Where the optical axis of the optical unit is deviated from the center line of the outer circumferential surface of the cylindrical member of the optical unit, the cylindrical member has a thick portion and a thin portion which are distributed in the circumferential direction. In general, the cylindrical member is made from a metal material such as stainless steel and its thermal expansion coefficient is much different from that of the transparent member made from glass or the like. Therefore, when the optical unit is put in a high-temperature atmosphere of autoclaving, stress is concentrated in the thick portion of the cylindrical member and the transparent member is rendered prone to peel off.

The present invention has been made in the above circumstances, and an object of the present invention is therefore to provide an optical unit which can be kept highly durable against a high-temperature atmosphere though having a structure that its optical axis is deviated from the center line of the outer circumferential surface of the cylindrical member, as well as an endoscope apparatus using it and a manufacturing method of such an optical unit.

The invention provides the following:

(1) An optical unit comprising:
a cylindrical member whose thickness varies in the circumferential direction;
a transparent member disposed at one end, in the axial direction, of the cylindrical member; and
a joining member which joins the transparent member to the cylindrical member and thereby seals the cylindrical member at the one end in the axial direction,
wherein a portion, joining a side surface of the transparent member to an inner circumferential surface of the cylindrical member, of the joining member is thicker at a position where the cylindrical member is thick than at a position where the cylindrical member is thin.

(2) An endoscope apparatus in which the optical unit according to item (1) is disposed in a tip portion of an endoscope insertion unit to be inserted into a subject body.

(3) A manufacturing method of an optical unit having a cylindrical member whose thickness varies in the circumferential direction and a transparent member disposed at one end, in the axial direction, of the cylindrical member, comprising:
producing a tentative assembly in which the transparent member is placed at one end, in the axial direction, of the cylindrical member and a joining member to serve for joining of the transparent member to the cylindrical member is placed between the transparent member and the cylindrical member; and
melting the joining member by heating the tentative assembly in a state that the axis of the cylindrical member is inclined from the vertical direction so that a thin portion of the cylindrical member becomes lower than a thick portion thereof.

The invention makes it possible to keep the optical unit highly durable against a high-temperature atmosphere, airtight, and watertight though it has a structure that its optical axis is deviated from the center line of the outer circumferential surface of the cylindrical member.

DESCRIPTION OF SYMBOLS

Figure 1:
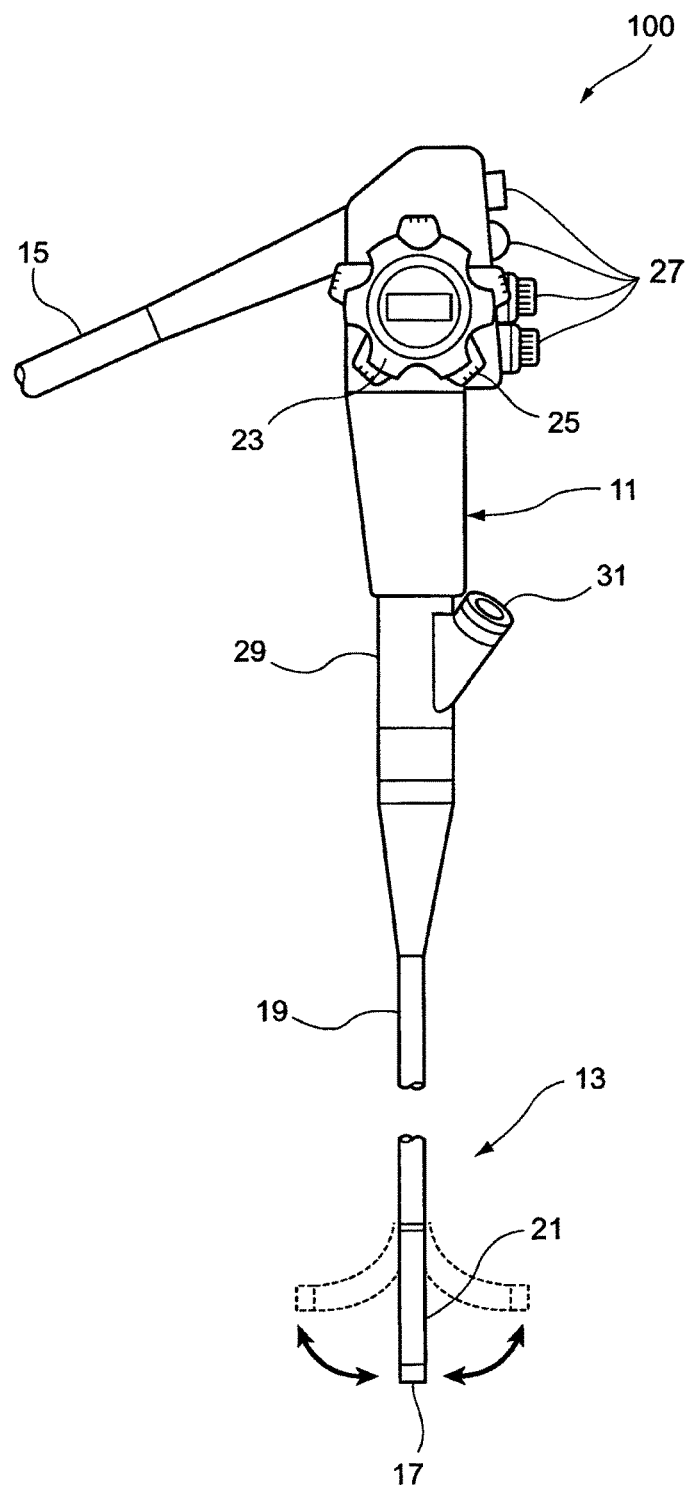
FIG. 1 is an overall view of an endoscope apparatus according to an embodiment of the present invention.

13: Endoscope insertion unit
45: Tip hard member
47: Hole
51: Cylindrical member
53: Cover glass (transparent member)
61: Imaging device
65: Outer circumferential surface
67: Inner circumferential surface
80: Metallized layer (primer film)
81: Side surface
83: (Inner) circumferential surface
85: Joining member
95: Flushing jig (frame-shaped jig)
100: Endoscope apparatus
200: Optical unit

DETAILED DESCRIPTION OF THE INVENTION

An embodiment of the present invention will be hereinafter described in detail with reference to the drawings. FIG. 1 is a view showing the configuration of an endoscope apparatus 100 according to the embodiment of the invention.

The endoscope apparatus 100, which is a medical apparatus, is equipped with a main body manipulation unit 11 and an endoscope insertion unit 13 which is continuous with the main body manipulation unit 11 and is to be inserted into a body cavity. A universal cord 15 is connected to the main body manipulation unit 11, and the tip of the universal cord 15 is provided with connectors (not shown) which are a lightguide connector and a video connector. The lightguide connector is connected detachably to a light source device (not shown) and thereby serves to supply illumination light to an illumination optical system of a tip portion 17 of the endoscope insertion unit 13. The video connector is connected detachably to a processor (not shown) which performs image signal processing etc. The video connector thus serves to take in a shot observation image.

The endoscope insertion unit 13 is composed of a soft portion 19, a curved portion 21, and the tip portion (hereinafter also referred to as an endoscope tip portion) 17 which are arranged in this order from the side of the main body manipulation unit 11. The curved portion 21 is bent remotely by manipulating (rotating) angled knobs 23 and 25, whereby the tip portion 17 can be directed to a desired direction.

The main body manipulation unit 11 is provided with various buttons 27 such as an air/water supply button, a suction button, and a release button in addition to the angled knobs 23 and 25. A link unit 29 which extends from the main body manipulation unit 11 and connects it to the endoscope insertion unit 13 is formed with a forceps hole 31 through an instrument for treatment such as forceps is to be inserted. The tip portion of an instrument that is inserted through the forceps hole 31 is guided by and put out of a forceps channel 33 (see FIG. 2).

Figure 2:
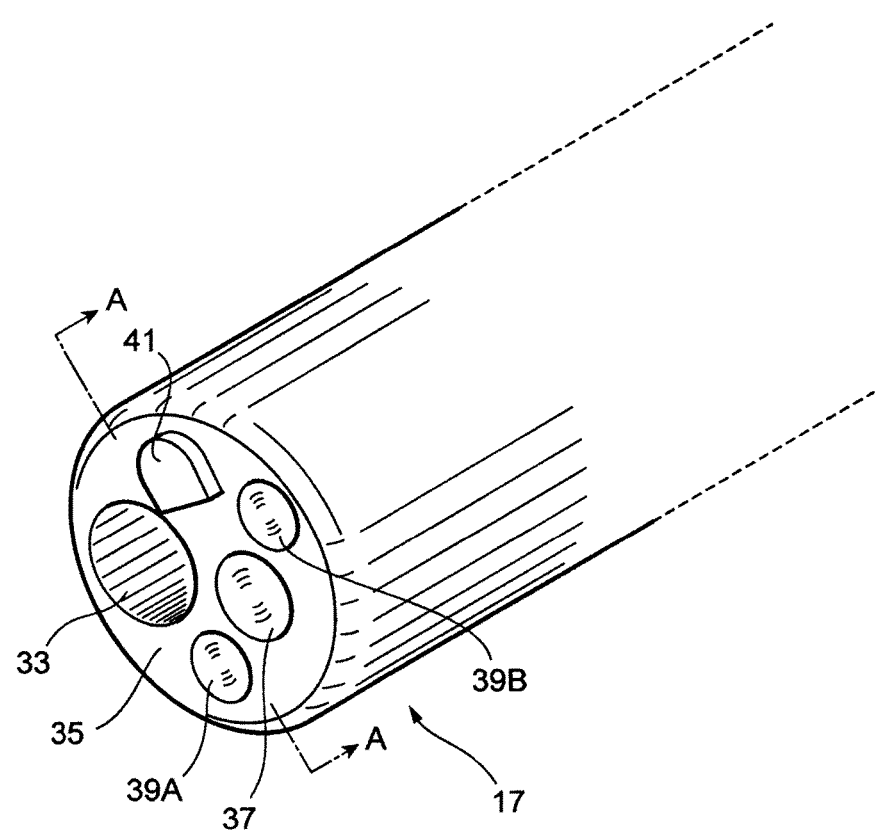
FIG. 2 is a schematic perspective view of an endoscope tip portion.

FIG. 2 is a schematic perspective view showing an appearance of the endoscope tip portion 17. An observation window 37 of an imaging optical system and illumination windows 39A and 39B of an illumination optical system are arranged in a tip surface 35 of the endoscope tip portion 17. The illumination windows 39A and 39B are located on the two respective sides of the observation window 37. Furthermore, the tip surface 35 is formed with openings of the forceps channel 33 and an air/water supply nozzle 41 for supplying air or water to the observation window 37.

Figure 3:
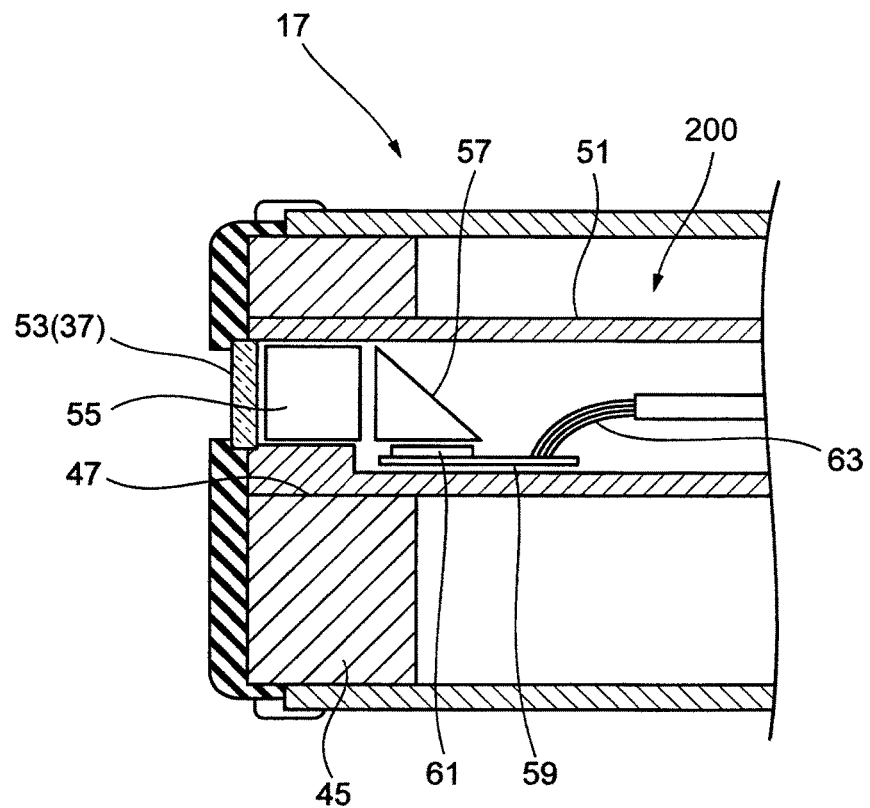
FIG. 3 is a schematic sectional view taken along line A-A in FIG. 2.

FIG. 3 is a schematic sectional view taken along line A-A in FIG. 2. The endoscope tip portion 17 has a tip hard member 45 which is made from a metal material such as stainless steel or ceramic. A cylindrical member 51 of an optical unit 200 of the imaging optical system is inserted in a hole 47 of the tip hard member 45 and fixed to the tip hard member 45 in a watertight manner. A cover glass 53 which is a transparent member is supported by one end portion, in the axial direction, of the cylindrical member 51 of the optical unit 200. The cover glass 53, which serves as the above-mentioned observation window 37, is made from sapphire glass or quartz glass.

An optical lens 55, a prism 57 for bending the optical axis by 90°, and an imaging device 61 which is mounted on a board 59 at the destination of the thus-bent optical axis are arranged inside the cylindrical member 51 in this order from the side of the cover glass 53. An imaging signal that is output from the imaging device 61 is transmitted from the board 59 to a control device (not shown) via a signal line 63.

As for each of the illumination windows 39A and 39B, as in the case of the observation window 37, a cylindrical member of an optical unit of the illumination optical system is inserted in the tip hard member 45 and fixed to the tip hard member 45 in a watertight manner.

<Structure of Optical Unit>

Figure 4:
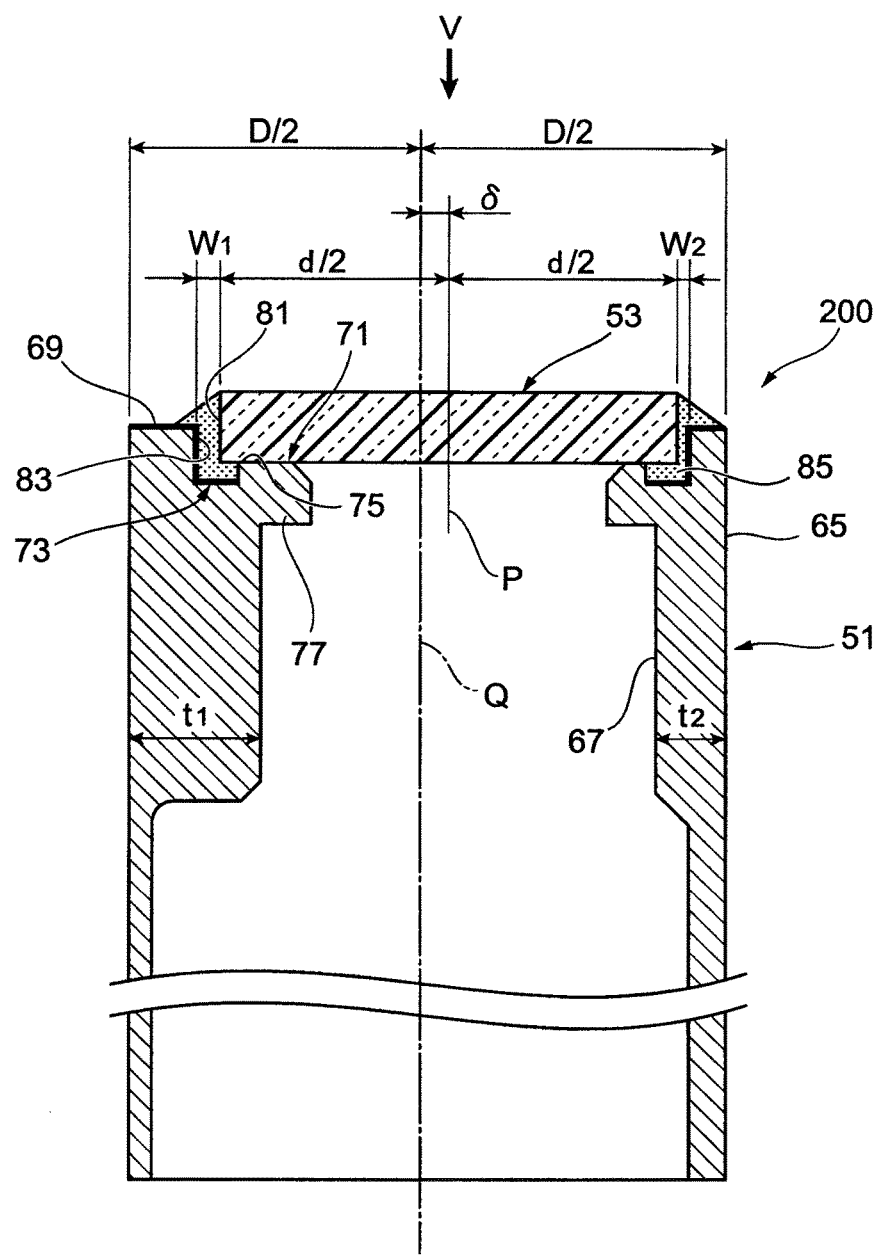
FIG. 4 is a sectional view of a structure including a cylindrical member and a cover glass of an optical unit.
Figure 5:
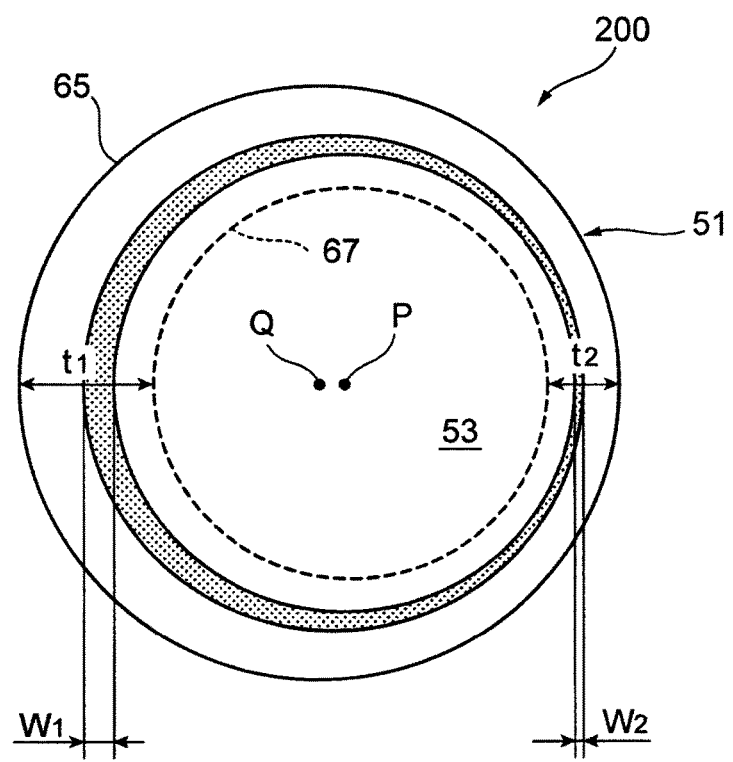
FIG. 5 is a view as viewed from the direction indicated by arrow V in FIG. 4.

FIG. 4 is a sectional view of a structure including the cylindrical member 51 and the cover glass 53 of the optical unit 200 of the imaging system. FIG. 5 is a view as viewed from the direction indicated by arrow V in FIG. 4. What are provided inside the cylindrical member 51 are not shown in FIGS. 4 and 5.

As shown in FIGS. 4 and 5, the thickness of one end portion, in the axial direction, of the cylindrical member 51 varies in the circumferential direction (the one end portion is located in a tip-side region of the endoscope tip portion 17). The center axis P of the disc-shaped cover glass 53 is deviated from the center axis Q of an outer circumferential surface 65 of the cylindrical member 51 by δ. The center axis of an inner circumferential surface 67 of the one end portion of the cylindrical member 51 is deviated from the center axis Q of its outer circumferential surface 65 by an amount corresponding to the deviation δ. Thus, the one end portion of the cylindrical member 51 has such a shape that its thickness varies continuously in the circumferential direction from a maximum thickness $t_1$ to a minimum thickness $t_2$. The cylindrical member 51 has the minimum thickness $t_2$ at a position that is opposite to a position where it has the maximum thickness $t_1$.

An end surface 69 of the one end portion of the cylindrical member 51 is formed, on its inner circumference side, with an annular stepped portion 71 which supports an outer peripheral portion of the cover glass 53. The stepped portion 71 has an annular groove 73 and a brim 77 which projects inward from the annular groove 73 toward the center axis Q and has a flat surface 75 which supports the cover glass 53.

Figure 6:
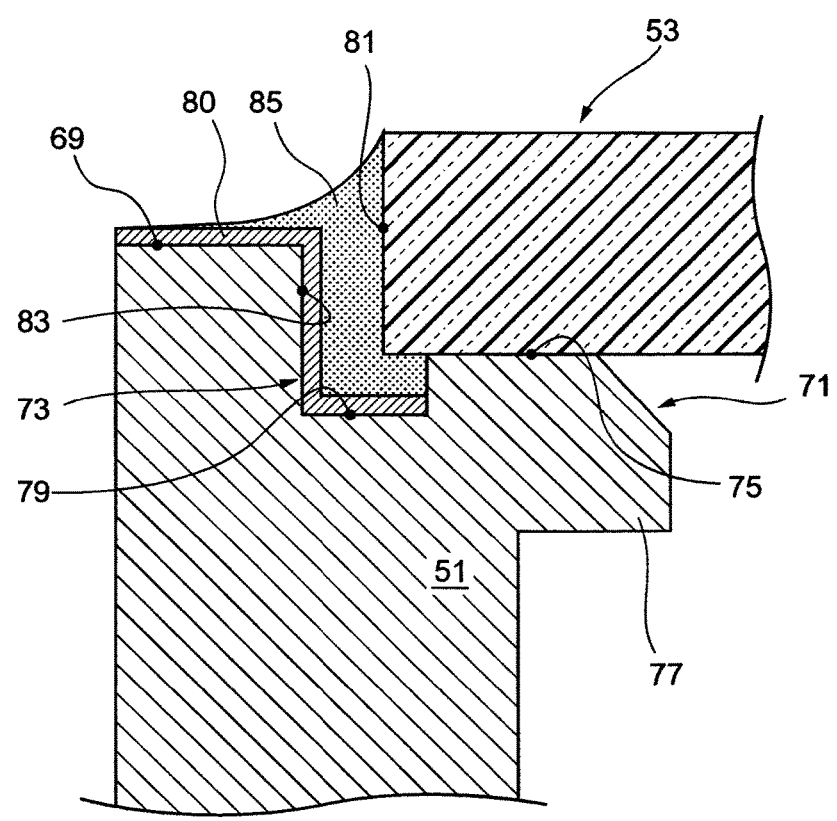
FIG. 6 is an enlarged sectional view of part of FIG. 4 that includes a stepped portion.

FIG. 6 is an enlarged sectional view of part of FIG. 4 that includes the stepped portion 71. The flat surface 75 of the brim 77 is lower than the end surface 69 of the cylindrical member 51 and higher than a bottom surface 79 of the annular groove 73, whereby a side surface 81 (outer circumferential surface) of the cover glass 53 faces a circumferential surface 83 of the annular groove 73.

The space between the side surface 81 of the cover glass 53 and the circumferential surface 83 of the annular groove 73 is filled with a joining member 85, whereby the side surface 81 and the circumferential surface 83 are joined to each other by the joining member 85. As shown in FIG. 4, as for the interval between the side surface 81 of the cover glass 53 and the circumferential surface 83 of the annular groove 73, that is, the radial thickness of the joining member 85, a thickness $W_1$ at a position where the cylindrical member 51 is thick is greater than a thickness $W_2$ at a position where the cylindrical member 51 is thin.

The joining member 85 is a joining layer of a brazing material which is formed by brazing. The material of the joining member 85 may be one or a combination of an Au—Sn alloy, solder, and various silver, copper, phosphor copper, bronze, palladium, and nickel-based brazing materials.

As shown in FIG. 6, an Ni/Au-plated metallized layer 80 is formed as a primer film on the end surface 69 of the cylindrical member 51 and the circumferential surface 83 and the bottom surface 79 of the annular groove 73. A metallized layer may also be formed on the side surface 81 (for joining to the joining member 85) and an end surface portion adjacent to it of the cover glass 53. The formation of the metallized layer (s) increases the wettability of the cylindrical member 51 with respect to the joining member 85 being in a melted state, whereby the brazing can be performed reliably and the airtightness and watertightness can be secured more reliably.

Instead of being parallel with the side surface 81 of the cover glass 53, the circumferential surface 83 of the annular groove 73 may be such a tapered surface as to increase the flowability of the joining member 85 being in a melted state.

With the optical unit 200 having the above structure, even if the endoscope apparatus 100 incorporating the optical unit 200 is subjected to high-pressure, high-temperature autoclaving, the cover glass 53 does not peel off the cylindrical member 51 and hence an event that steam or liquid goes into the optical unit 200 can be prevented.

Figure 7:
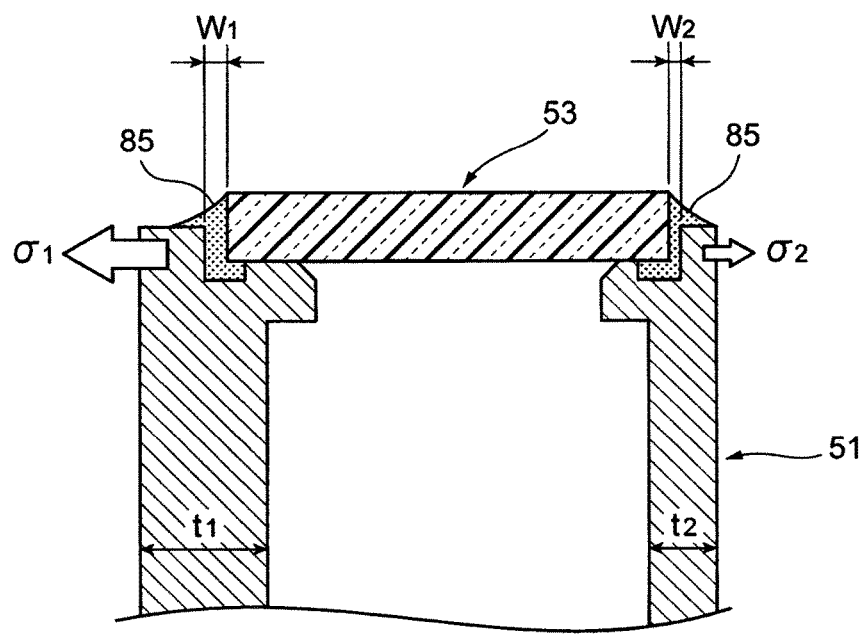
FIG. 7 schematically illustrates how thermal stress acts on the cylindrical member when the optical unit is exposed to a high-temperature atmosphere.

FIG. 7 schematically illustrates how thermal stress acts on the cylindrical member 51 when the optical unit 200 is exposed to a high-temperature atmosphere. When the optical unit 200 is exposed to a high-temperature atmosphere, thermal stress occurs due to a difference between the linear expansion coefficients of the materials of the cylindrical member 51 and the cover glass 53 of the optical unit 200. The thicker the cylindrical member 51, the stronger the thermal stress. Highest thermal stress $\sigma_1$ acts on the portion having the maximum thickness $t_1$, and thermal stress $\sigma_2$ which is lower than $\sigma_1$ acts on the portion having the minimum thickness $t_2$. In this manner, stress concentration occurs in the portion having the maximum thickness $t_1$ and hence the optical unit 200 is particularly prone to peel off the cylindrical member 51 there unless a proper countermeasure is taken.

In the optical unit 200 according to the embodiment, the joining member 85 is made thicker ($W_1 > W_2$) as the thickness of the associated portion of the cylindrical member 51 increases. Therefore, even if thermal stress acts on the thick portion of the cylindrical member 51 due to a temperature variation, it is weakened by the thick portion, having the thickness $W_1$, of the joining member 85 which is softer than the cylindrical member 51 and the cover glass 53. As a result, peeling hardly occurs at the interface between the cylindrical member 51 and the joining member 85 and the interface between the cover glass 53 and the joining member 85, whereby the optical unit 200 can be kept airtight and watertight in a stable manner. As a result, an optical unit can be obtained which can be kept highly durable against a high-temperature atmosphere though having the structure that its optical axis is deviated from the center line of the outer circumferential surface of the cylindrical member 51.

<Manufacturing Method of Optical Unit>

Next, a description will be made of the brazing of the optical unit 200. However, the brazing process described below is just an example and the invention is not limited to it.

Figure 8:
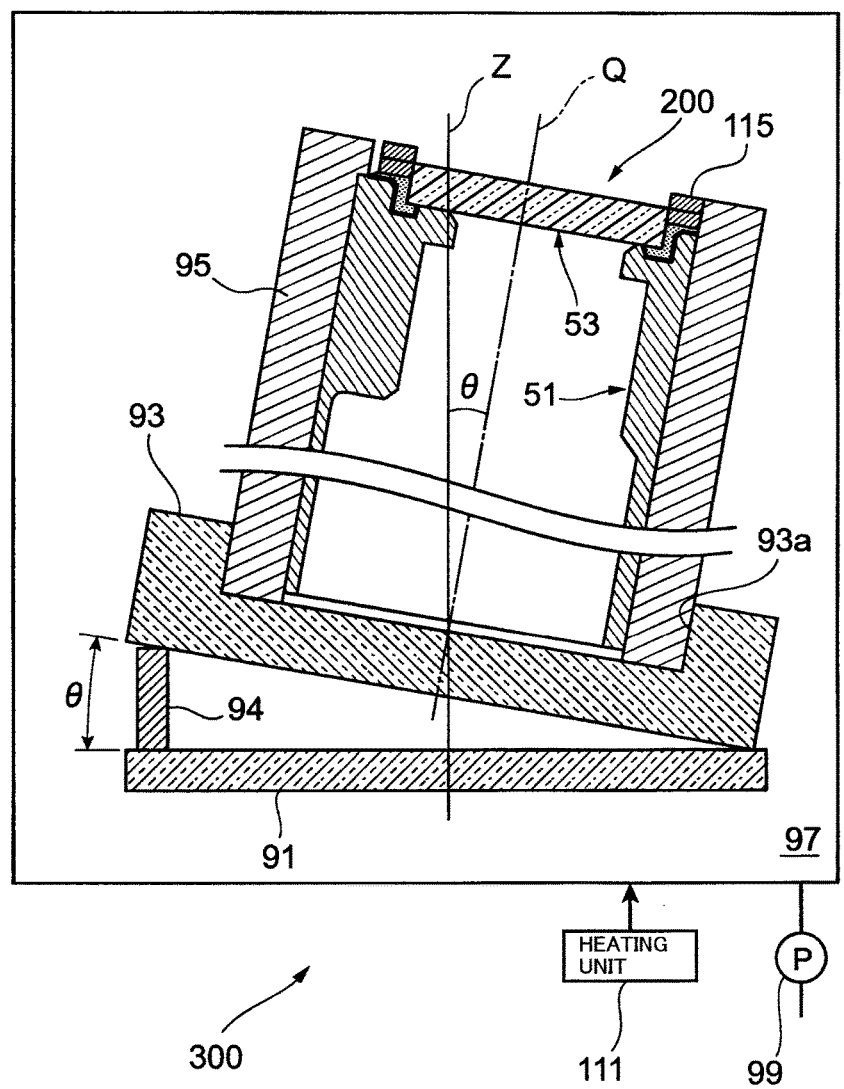
FIG. 8 schematically illustrates the configuration of a vacuum brazing machine for joining the cover glass of the optical unit to its cylindrical member.

FIG. 8 schematically illustrates the configuration of a vacuum brazing machine 300 for joining the cover glass 53 of the optical unit 200 to its cylindrical member 51. The vacuum brazing machine 300 is composed of a base 91 which is installed horizontally; an inclinable plate 93 which is mounted on the base 91 in an inclinable manner; a drive mechanism 94 for driving (inclining) the inclinable plate 93; a cylindrical flushing jig (frame-shaped jig) 95 for supporting the optical unit 200 indirectly by means of its inner circumferential surface; a vacuum chamber 97 for housing the base 91, the inclinable plate 93, and the flushing jig 95; a vacuum pump 99 for reducing the pressure inside the vacuum chamber 97; and a heating unit 111 for heating the inside of the vacuum chamber 97. The drive mechanism 94, the vacuum chamber 97, and the heating unit 111 are drive-controlled by a control unit (not shown).

The inclinable plate 93 has a recessed support portion 93a for supporting the flushing jig 95. By driving the drive mechanism 94, the flushing jig 95 which supports the optical unit 200 can be held by the inclinable plate 93 in such a manner that the optical unit 200 is inclined by a desired angle θ.

The shape of the flushing jig 95 is not limited to the cylindrical shape; it suffices that the flushing jig 95 be a frame-shaped body whose inner circumferential surface is shaped so as to conform to the outer circumferential shape of the cylindrical member 51.

The heating unit 111 may be a high-frequency heating device, a resistive heating device, of the like capable of heating the inside of the vacuum chamber 97.

A description will be made of a specific procedure for brazing the optical unit 200 using the vacuum brazing machine 300. First, the cylindrical member 51 is inserted into the flushing jig 95 and the cover glass 53 is placed on the cylindrical member 51 at one end in the axial direction. An Au—Sn alloy foil 115 (member for joining) is then set adjacent to the outer circumferential surface of the cover glass 53. If necessary, plural Au—Sn alloy foils 115 are set so that a necessary filling volume can be obtained. As a result, a tentative assembly of the cylindrical member 51, the cover glass 53, and the Au—Sn alloy foil 115 is set in the flushing jig 95.

Subsequently, the control unit drives the drive mechanism 94 to incline the inclinable plate 93 which supports the flushing jig 95 so that the thin portion of the cylindrical member 51 becomes lower than its thick portion. As a result, the tentative assembly comes to assume a state that the center axis Q of the outer circumferential surface of the cylindrical member 51 is inclined from the line (vertical line) Z normal to the base 91 by an inclination angle θ. The tentative assembly in this state is placed in the vacuum chamber 97. The inclination angle θ is set to a proper value in a range of 5° to 45°, preferably 7° to 15°. The Au—Sn alloy foil 115 is in contact with the lower part of the inner circumferential surface of the inclined flushing jig 95 and hence is not deviated when, for example, the tentative assembly is moved into the vacuum chamber 97.

The vacuum chamber 97 is then closed up tightly in the state that the tentative assembly supported by the flushing jig 95 is set in the vacuum chamber 97. The control unit drives the vacuum pump 99 and thereby reduces the pressure inside the vacuum chamber 97 to 10 Pa or less, for example.

After the pressure inside the vacuum chamber 97 has been reduced to a desired value, the control unit drives the heating unit 111 to heat the inside of the vacuum chamber 97. The target heating temperature is set at, for example, about 300° C. to 400° C. and the temperature increase rate is set at about 1 to 3° C./min. The target heating temperature is held for about 3 to 10 minutes.

The heated Au—Sn alloy foil 115 is melted and flows into the space between the inner circumferential surface of the cylindrical member 51 and the side surface 81 of the cover glass 53. Because of its surface tension, the joining member 85 in liquid form that has flowed into and filled up the space exerts attractive force that is directed outward in the radial direction on the side surface 81 of the cover glass 53 over the entire circumference of the cover glass 53. The cover glass 53 is rendered stationary at a balancing position of forces including the attractive force. Since the attractive force produced by the surface tension of the joining member 85 is stronger than frictional force that the cover glass 53 receives from flat surface 75 of the stepped portion 71, the cover glass 53 is rendered in a state that it can move easily in the radial direction. That is, in this state, the cover glass 53 which is placed in the melted joining member 85 is in a free support state that it can move in the radial direction.

Since the cover glass 53 is in the free support state and the cylindrical member 51 is inclined, the optical unit 200 is shifted downward and rendered stationary there being influenced by gravity though the inclination angle θ is small.

After a lapse of the heating holding time, the control unit causes the inside of the vacuum chamber 97 to be cooled gradually. The melted joining member 85 solidifies gradually. As a result, the cover glass 53 is joined to the cylindrical member 51 in a state that the thickness $W_1$ of the joining member 85 at the position where the cylindrical member 51 is thick is greater than the thickness $W_2$ of the joining member 85 at the position where the cylindrical member 51 is thin.

After the gradual cooling, the vacuum chamber 97 is opened to the atmosphere and the assembly in which the cover glass 53 has been joined to the cylindrical member 51 is taken out of the vacuum chamber 97. The optical unit 200 as shown in FIG. 4 is obtained by brazing the cover glass 53 according to the above-described procedure. Since the cover glass 53 can be joined to the cylindrical member 51 stably even with a small joining area, the cover glass 53 can be thinned further and hence it becomes easier to increase the angle of view and the illumination angle that relate to the optical unit 200.

Other Example Structures

Other example structures of the optical unit will be described below.

Figure 9:
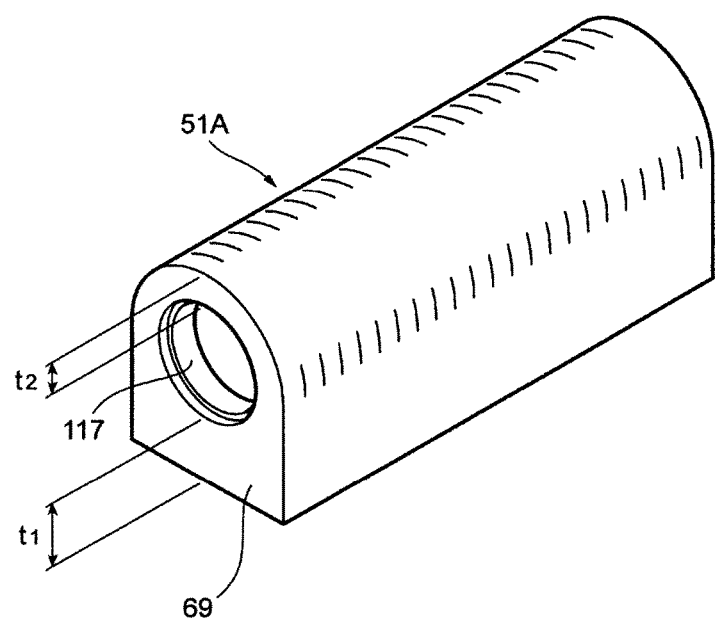
FIG. 9 is a perspective view of a cylindrical member having another structure.

FIG. 9 is a perspective view of a cylindrical member 51A having another structure. Although the above-described cylindrical member 51 has the cylindrical external shape, the external shape of the cylindrical member is not limited to it. In the cylindrical member 51A shown in FIG. 9, one end surface 69 in the axial direction is formed with an opening 117 in which a cover glass is inserted. The portion of the end surface 69 that is located above the opening 117 (as view in FIG. 9) is circular, and the portion below the opening 117 is angled. The distance between the outer circumferential surface of the cylindrical member 51A and the circumferential surface of the opening 117 (i.e., the thickness of the cylindrical member 51A) varies depending on the circumferential position of the opening 117; the length $t_1$ of the angled portion of the end surface 69 is greater than the length $t_2$ of its circular portion.

The cover glass can be joined to the above-configured cylindrical member 51A in the same manner as described above, whereby the degree of thermal stress concentration in the thick portion of the cylindrical member 51A can be lowered.

Figure 10:
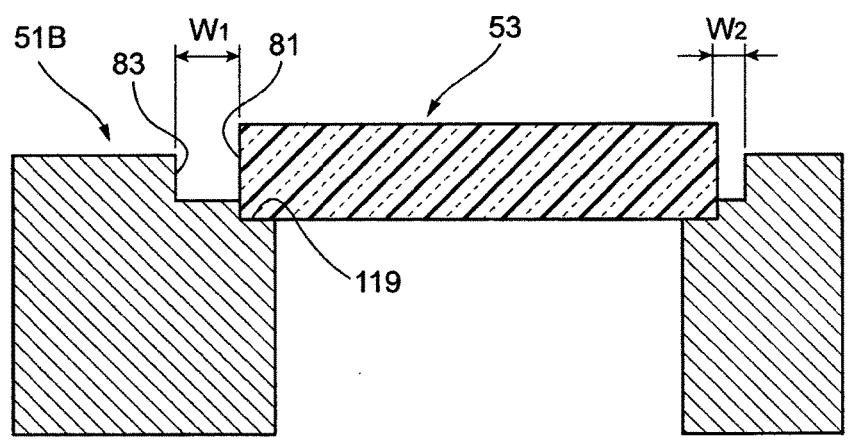
FIG. 10 is a sectional view of a cylindrical member having a further structure.

FIG. 10 is a sectional view showing the structure of a cylindrical member 51B having a further structure. Although the above-described cylindrical member 51 is such that the cover glass 53 is deviated from the center axis of the outer circumferential surface of the cylindrical member 51 by inclining the cylindrical member 51 in the heating step, the invention is not limited to such a case. In the cylindrical member 51B shown in FIG. 10, the fixing position of a cover glass 53 is determined by a groove 119 which is formed in the cylindrical member 51B. The cover glass 53 is fitted into the groove 119, whereby the interval between an inner circumferential surface 83 of the cylindrical member 51B and the cover glass 53 is longer on the side where the cylindrical member 51B is thick than on the side where the cylindrical member 51B is thin.

With the cylindrical member 51B having the above structure, the cover glass 53 can be deviated from the center axis of the outer circumferential surface of the cylindrical member 51B without the need for inclining the cylindrical member 51B in a heating step.

Figure 11A:
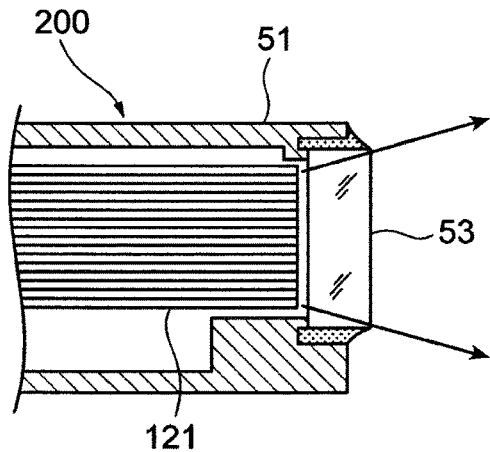
FIGS. 11A, 11B and 11C are schematic sectional views showing example configurations of the optical unit of an illumination optical system.
Figure 11B:
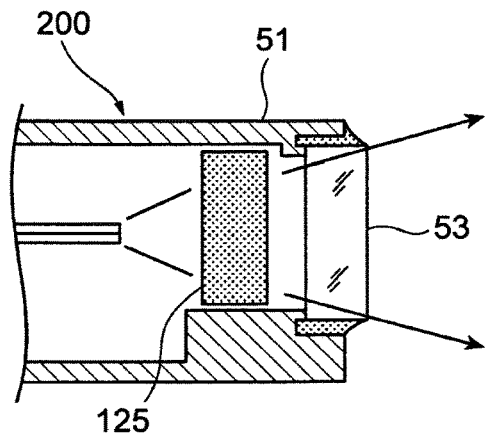
Figure 11C:
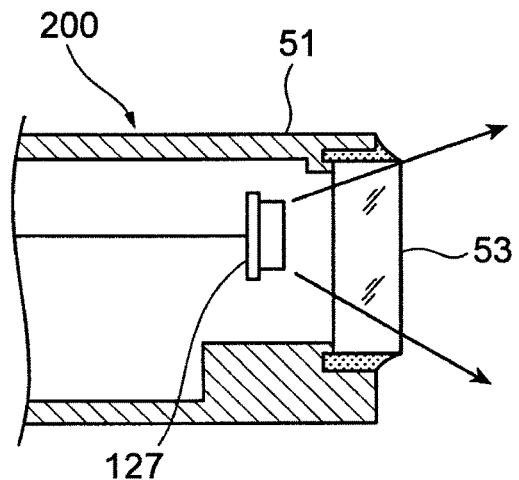

FIGS. 11A-11C are schematic sectional views showing example configurations of the optical unit 200 of the illumination optical system. FIG. 11A shows an example configuration in which a lightguide 121 which is a bundle of optical fibers and serves to guide illumination light emitted from a light source is disposed inside the optical unit 200. FIG. 11B shows an example configuration in which a single-mode or multi-mode optical fiber 123 and a phosphor 125 which is disposed close to the light exit end of the optical fiber 123 and emits light when excited by light that is guided by the optical fiber 123 are disposed inside the optical unit 200. FIG. 11C shows an example configuration in which a semiconductor light-emitting element 127 is disposed inside the optical unit 200.

In either example configuration, the optical axis of illumination light is deviated from the center axis of the outer circumferential surface of the cylindrical member 51. When the optical unit 200 is inserted into the tip hard member 45 of the endoscope tip portion 17, the position of the optical axis of illumination light can be fine-adjusted easily by rotating the cylindrical member 51. When the endoscope apparatus 100 is subjected to high-pressure, high-temperature autoclaving sterilizing treatment, the cover glass 53 does not peel off the cylindrical member 51 and hence introduction of steam or water into the optical unit 200 can be prevented.

EXAMPLES

Next, a description will be made of Example of the joining of the cover glass 53 of the optical unit 200 shown in FIG. 5 to its cylindrical member 51.

In this Example, the cylindrical member 51 was a cylindrical sleeve which was made from stainless steel and had an outer diameter 3 mm. The maximum thickness difference $(t_1-t_2)$ of the portion into which the cover glass 53 was inserted was 0.12 mm. The end surface 69 of the cylindrical member 51 and the circumferential surface 83 and the bottom surface 79 of the annular groove 73 on which brazing was to be performed had been subjected to Ni/Au plating.

The cover glass 53 was made from sapphire glass and was 2.5 mm in diameter and 0.3 mm in thickness. A pile of two annular Au—Sn foils 115 (Au: 20 wt %) each being 0.1 mm in thickness was used as a brazing material.

As for the use conditions of the vacuum brazing machine 300, the target degree of vacuum inside the vacuum chamber 97 was 10 Pa or less and the heating schedule was such that the heating temperature was increased from room temperature to 350° C. (target temperature) in 2 hours, held at 350° C. for 5 minutes, and decreased naturally in one night. At the time of joining, the inclination angle of the cylindrical member 51 with respect to the vertical direction was set at 10°.

Brazing was performed under the above conditions to complete an optical unit 200. The cover glass 53 was joined to the cylindrical member 51 in such a manner that the center axis of the cover glass 53 was deviated from the center axis of the outer circumferential surface of the cylindrical member 51. A resulting joining member 85 of the brazing material was thick at the position corresponding to the thick portion of the cylindrical member 51 and was thin at the position corresponding to the thin portion of the cylindrical member 51. The optical unit 200 thus produced was heated in a high-temperature atmosphere that is similar to one used in autoclaving sterilizing treatment. No stress concentration was found and the joining of the cover glass 53 and the cylindrical member 51 was kept satisfactorily.

The invention is not limited to the above embodiment. Combining components used in the embodiment and acts of those skilled in the art of modifying or applying the embodiment based on the disclosure of the specification and known techniques are possible as extensions of the embodiment and should be included in the scope of protection of the invention.

For example, the above-described cover glass 53 may be a lens. As for the timing of inclining the cylindrical member 51 to perform brazing, the cylindrical member 51 need not always be inclined when it is placed in the flushing jig 95 (see FIG. 8). The cylindrical member 51 may be set parallel with the vertical direction when placed in the flushing jig 95 and inclined at a proper time after a start of heating by driving the drive mechanism 94. In this case, the joining member 85 is apt to fill the entire joining space with a higher level of uniformity. Heating need not always be performed in a vacuum atmosphere; anti-oxidation heat treatment such as heating in an inert gas (e.g., nitrogen gas) atmosphere may be employed.

As described above, this specification discloses the following items:

(1) An optical unit comprising:

a cylindrical member whose thickness varies in the circumferential direction;

a transparent member disposed at one end, in the axial direction, of the cylindrical member; and a joining member which joins the transparent member to the cylindrical member and thereby seals the cylindrical member at the one end in the axial direction, wherein a portion, joining a side surface of the transparent member to an inner circumferential surface of the cylindrical member, of the joining member is thicker at a position where the cylindrical member is thick than at a position where the cylindrical member is thin.

(2) The optical unit according to item (1), wherein the center axis of the transparent member is deviated from the center axis of an outer circumferential surface of the cylindrical member.

(3) The optical unit according to item (1) or (2), wherein the joining member is made from a brazing material.

(4) The optical unit according to any one of items (1) to (3), wherein:

an end surface, located at the one end in the axial direction, the cylindrical member is formed with an annular stepped portion on an inner circumference side;

the stepped portion is formed with a brim which supports an outer peripheral portion of the transparent member and an annular groove in which the joining member is placed; and an interval between the side surface of the transparent member and the inner circumferential surface of the cylindrical member is longer at the position where the cylindrical member is thick than at the position where the cylindrical member is thin.

(5) The optical unit according to any one of items (1) to (4), wherein the cylindrical member houses imaging optical members for taking an observation image through the transparent member.

(6) The optical unit according to any one of items (1) to (5), wherein the cylindrical member houses illumination optical members for emitting illumination light through the transparent member.

(7) An endoscope apparatus in which the optical unit according to any one of items (1) to (6) is disposed in a tip portion of an endoscope insertion unit to be inserted into a subject body.

(8) A manufacturing method of an optical unit having a cylindrical member whose thickness varies in the circumferential direction and a transparent member disposed at one end, in the axial direction, of the cylindrical member, comprising the steps of:

producing a tentative assembly in which the transparent member is placed at one end, in the axial direction, of the cylindrical member and a joining member to serve for joining of the transparent member to the cylindrical member is placed between the transparent member and the cylindrical member; and melting the joining member by heating the tentative assembly in a state that the axis of the cylindrical member is inclined from the vertical direction so that a thin portion of the cylindrical member becomes lower than a thick portion thereof.

(9) The manufacturing method of an optical unit according to item (8), further comprising the step of joining the transparent member to the cylindrical member by causing the melted joining member to solidify and thereby sealing the cylindrical member at the one end in the axial direction.

(10) The manufacturing method of an optical unit according to item (8) or (9), wherein the melting step is executed in a vacuum atmosphere or an inert gas atmosphere.

(11) The manufacturing method of an optical unit according to any one of items (8) to (10), wherein in the melting step, the tentative assembly is placed inside a frame of a frame-shaped jig, and the frame-shaped jig is inclined from the vertical direction.

(12) The manufacturing method of an optical unit according to any one of items (8) to (11), wherein a primer film for increasing wettability with respect to the melted joining member is formed on the cylindrical member in a region of joining to the transparent member.

What is claimed is:

1. An optical unit comprising:
   a cylindrical member whose thickness varies in a circumferential direction;
   a transparent member disposed at one end, in an axial direction, of the cylindrical member; and
   a joining member which joins the transparent member to the cylindrical member and thereby seals the cylindrical member at the one end in the axial direction,
   wherein a portion, joining a side surface of the transparent member to an inner circumferential surface of the cylindrical member, of the joining member has radially a thicker portion adjoining where the cylindrical portion is thick and a thinner portion adjoining where the cylindrical member is thin,
   wherein an end surface, located at the one end in the axial direction of the cylindrical member, is formed with an annular stepped portion on an inner circumference side of the end surface,
   wherein the stepped portion is formed with a brim which supports an outer peripheral portion of the transparent member and an annular groove which is provided between the brim and a part, other than the brim, of the cylindrical member in the circumferential direction and in which a part of the joining member is placed,
   wherein the part of the joining member placed in the annular groove is in contact with a part of a surface, at an other end in the axial direction, of the transparent member, and
   wherein an interval between the side surface of the transparent member and the inner circumferential surface of the cylindrical member is longer at the position where the cylindrical member is thick than at the position where the cylindrical member is thin.

2. The optical unit according to claim 1, wherein a center axis of the transparent member is deviated from a center axis of an outer circumferential surface of the cylindrical member.

3. The optical unit according to claim 1, wherein the joining member is made from a brazing material.

4. The optical unit according to claim 1, wherein the cylindrical member houses imaging optical members for taking an observation image through the transparent member.

5. The optical unit according to claim 1, wherein the cylindrical member houses illumination optical members for emitting illumination light through the transparent member.

6. An endoscope apparatus in which the optical unit according to claim 1 is disposed in a tip portion of an endoscope insertion unit to be inserted into a subject body.

* * * * *